(12) United States Patent
Ooms et al.

(10) Patent No.: US 8,518,231 B2
(45) Date of Patent: Aug. 27, 2013

(54) PROCESS FOR PRODUCTION OF DIARYL CARBONATE

(75) Inventors: Pieter Ooms, Krefeld (DE); Andreas Bulan, Langenfeld (DE); Johann Rechner, Kempen (DE); Rainer Weber, Odenthal (DE); Marc Buts, Duffel (BE); Johan Vanden Eynde, Zwijnaarde (BE)

(73) Assignee: Bayer Intellectual Property GmbH (DE)

( * ) Notice: Subject to any disclaimer, the term of this patent is extended or adjusted under 35 U.S.C. 154(b) by 0 days.

(21) Appl. No.: 13/037,909

(22) Filed: Mar. 1, 2011

(65) Prior Publication Data

US 2011/0147229 A1 Jun. 23, 2011

Related U.S. Application Data

(63) Continuation of application No. 12/328,434, filed on Dec. 4, 2008, now abandoned.

(30) Foreign Application Priority Data

Dec. 6, 2007 (DE) .......................... 10 2007 058 701

(51) Int. Cl.
*C25B 1/16* (2006.01)
*C25B 1/34* (2006.01)
*C25C 1/02* (2006.01)
*C07C 69/96* (2006.01)
*C07C 51/58* (2006.01)

(52) U.S. Cl.
USPC ........... 205/516; 205/510; 205/620; 558/260; 558/274; 562/847

(58) Field of Classification Search
USPC ................. 558/260, 274; 562/847; 205/742, 205/746, 748, 749, 510, 516, 620
See application file for complete search history.

(56) References Cited

U.S. PATENT DOCUMENTS

| 3,017,424 | A | * | 1/1962 | Meyer et al. ................... 558/274 |
| 3,773,634 | A | | 11/1973 | Stacey et al. |
| 4,016,190 | A | * | 4/1977 | Bockmann et al. ........... 558/271 |
| 4,025,405 | A | | 5/1977 | Dotson et al. |
| 5,340,905 | A | | 8/1994 | Kühling et al. |
| 5,734,004 | A | | 3/1998 | Kühling et al. |
| 6,291,598 | B1 | * | 9/2001 | Williams et al. ............... 525/467 |
| 6,340,736 | B1 | * | 1/2002 | Coenen et al. ................. 528/196 |
| 6,348,613 | B2 | * | 2/2002 | Miyamoto et al. ............ 558/274 |
| 6,531,623 | B2 | | 3/2003 | Chrisochoou et al. |
| 6,548,691 | B2 | | 4/2003 | Alewelt et al. |
| 6,680,400 | B2 | | 1/2004 | Alewelt et al. |
| 2003/0155301 | A1 | | 8/2003 | Silva et al. |
| 2005/0115901 | A1 | * | 6/2005 | Heuser et al. ................. 210/639 |
| 2006/0047170 | A1 | | 3/2006 | Keggenhoff et al. |
| 2008/0053836 | A1 | * | 3/2008 | Bulan et al. ................... 205/338 |

FOREIGN PATENT DOCUMENTS

| CA | 2375245 A1 | 12/2000 |
| DE | 10 2004 041 777 A1 | 3/2006 |
| EP | 0541114 A2 | 5/1993 |
| EP | 0784048 A1 | 7/1997 |
| EP | 1216981 A2 | 6/2002 |
| EP | 1216982 A2 | 6/2002 |
| EP | 1219589 A1 | 7/2002 |
| EP | 1200359 B1 | 2/2004 |
| EP | 1 894 914 A2 | 3/2008 |
| GB | 1500288 A | 2/1978 |
| GB | 1500288 A * | 2/1978 |
| JP | 10081986 A | 2/1998 |
| JP | 10081986 A * | 3/1998 |
| RU | 2007 132 823 A | 3/2009 |
| WO | WO 00/78682 A1 | 12/2000 |
| WO | WO-01/38419 A1 | 5/2001 |
| WO | WO-03/070639 A1 | 8/2003 |

* cited by examiner

*Primary Examiner* — Edna Wong
(74) *Attorney, Agent, or Firm* — Novak Druce Connolly Bove + Quigg LLP

(57) ABSTRACT

The invention relates to a process for production of diaryl carbonate combined with the electrolysis of the resultant alkali metal chloride-containing process wastewater. The process according to the invention makes possible, inter alia, improved utilization in electrolysis of the alkali metal chloride-containing solution obtained in the production of diaryl carbonate.

19 Claims, No Drawings

PROCESS FOR PRODUCTION OF DIARYL CARBONATE

RELATED APPLICATIONS

This application is a continuation of U.S. patent application Ser. No. 12/328,434, filed Dec. 4, 2008, now abandoned, which claims benefit to German Patent Application No. 10 2007 058701.7, which is incorporated herein by reference in its entirety for all useful purposes.

BACKGROUND OF THE INVENTION

The invention relates to a process for production of diaryl carbonate combined with the electrolysis of the resultant alkali metal chloride-containing process wastewater. The process according to the invention makes possible, inter alia, improved utilization in electrolysis of the alkali metal chloride-containing solution obtained in the production of diaryl carbonate.

The production of diaryl carbonates (diaryl carbonate) proceeds conventionally by a continuous process, by production of phosgene and subsequent reaction of monophenols and phosgene in an inert solvent in the presence of alkali and a basic nitrogen catalyst in the interface.

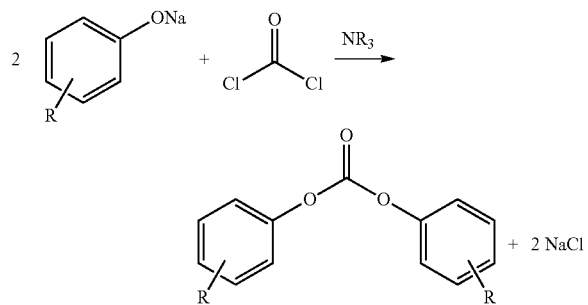

The production of diaryl carbonates, for example by the phase boundary process, is described in principle in the literature, see, for example, in Chemistry and Physics of Polycarbonates, Polymer Reviews, H. Schnell, Vol. 9, John Wiley and Sons, Inc. (1964), pp. 50/51.

U.S. Pat. No. 4,016,190 describes a production process for diaryl carbonates which is operated at temperatures >65° C. The pH in this process is first set to be low (pH 8 to 9) and subsequently high (10 to 11).

Optimization of the process by improving the mixing, and maintaining a narrow temperature and pH profile, and also isolation of the product, are described in EP 1 219 589 A1, EP 1 216 981 A2, EP 1 216 982 A2 and EP 784 048 A1.

However, in these known processes, a high residual phenol value in the wastewater of these processes, which can pollute the environment and give the effluent treatment plants increased wastewater problems, makes complex purification operations necessary. For instance, WO 03/070639 A1 describes removal of the organic impurities in wastewater by an extraction with methylene chloride.

Conventionally, alkali metal chloride-containing, preferably sodium-chloride-containing, solution is freed from solvents and organic residues and must then be disposed of.

However, it is also known that purification of the sodium-chloride-containing waste-waters can proceed according to EP 1 200 359 A1 or U.S. Pat. No. 6,340,736 via ozonolysis and is then suitable for use in sodium chloride electrolysis. A disadvantage of ozonolysis is that this process is very cost intensive.

According to EP 541 114 A2, a sodium-chloride-containing wastewater stream is evaporated up to complete removal of the water and the remaining salt having the organic impurities is subject to a thermal treatment, as a result of which the organic components are destroyed. Particular preference here is given to the use of infrared radiation. A disadvantage of the process is that the water must be completely evaporated so that the process cannot be carried out economically.

According to WO 03/70639 A1, the wastewater from a DPC production is purified by extraction and then fed to the sodium chloride electrolysis. However, by means of the process described, only a maximum of 26% of the sodium chloride can be recovered from the wastewater of the DPC production, since, at higher feed rates, the water introduced into the electrolysis together with the wastewater would bring the water balance of the sodium chloride electrolysis out of equilibrium.

The alkali-metal-chloride-containing, preferably sodium-chloride-containing, solutions which are obtained in DPC production, typically have an alkali metal chloride content, preferably sodium chloride content, of 13 to 17% by weight. It is not possible thereby to recover all of the alkali metal chloride present in the solutions in this manner. At an alkali metal chloride concentration of 17% by weight, in the standard alkali metal chloride electrolysis, preferably standard sodium chloride electrolysis, using a commercially available ion-exchange membrane which exhibits a water transport of 3.5 mol of water per mole of sodium, only the use of approximately 23% of the sodium chloride from the sodium-chloride-containing solutions succeeds. Even with concentration up to a saturated sodium chloride solution of approximately 25% by weight only give a recycling rate of 38% of the sodium chloride contained in the sodium-chloride-containing solution. Complete recycling of the alkali-metal-chloride-containing solution is not known to date. According to WO 01/38419 A1, the sodium-chloride-containing solution can be evaporated by means of thermal processes, so that a highly concentrated sodium chloride solution can be fed to the electrolysis cell. However, the evaporation is energy intensive and expensive.

Proceeding from the above-described prior art, the object of the invention was to provide a process for production of diaryl carbonate which delivers products in high purity and good yield and at the same time makes possible reduction of the environmental pollution and/or wastewater problems in the sewage treatment plants by maximal recycling of alkali metal chloride from alkali-metal-chloride-containing process wastewater solutions which are obtained from the diaryl carbonate production.

In particular, in the recycling, it should be taken into account that the reaction of alkali metal chloride, preferably sodium chloride, to give chlorine and alkali solution, preferably sodium hydroxide solution, and optionally hydrogen, should proceed with minimum energy use and therefore likewise be sparing of resources.

It has surprisingly been found that in the production of diaryl carbonates by reaction of monophenols and phosgene in an inert solvent in the presence of a base and optionally a basic catalyst, improved utilization of the alkali-metal-chloride-containing solution resulting from the production of the diaryl carbonate can be achieved in a chlor-alkali electrolysis, when the alkali-metal-chloride-containing solution resulting from the production of diaryl carbonates has an alkali metal chloride content of 18 to 25% by weight, based on the total weight of the alkali-metal-chloride-containing solution. Such an alkali metal chloride content of 18 to 25% by weight of the alkali-metal-chloride-containing solution which is obtained in the production of diaryl carbonates can be achieved according to the invention firstly by the means that, in the reaction of monophenol and phosgene in the presence of a base, the monophenol and an alkali-metal-containing base are used in amounts such that the sodium phenolate content of the resultant solution of alkali-metal-containing base and monophenol is in a specially selected range, preferably 31 to 40% by weight sodium phenolate, based on the total weight of the solution. In addition, or alternatively, at least a part of the alkali-metal-chloride-containing solution which is obtained in the production of diaryl carbonates can be recycled to the production of diaryl carbonates, for example by replacing any water to be used in order likewise to achieve concentration of the alkali-metal-chloride-containing solution obtained in the production of diaryl carbonates to an alkali metal chloride content of 18 to 25% by weight.

This is surprising, since an elevation of the sodium phenolate content in the starting solution in the production of diaryl carbonates in the subsequent exothermal formation of diaryl carbonates should lead to an increased occurrence of energy and consequently to increased by-product formation. In addition, in the recycling of the sodium-chloride-containing solution to the diaryl carbonate production, for example by replacing any water to be used, owing to the presence of alkali metal chloride in the starting material solution, a decrease in the solubility of phenol and corresponding precipitation must be expected. Surprisingly, neither were observed within the range selected according to the invention of an alkali metal chloride content of 18 to 25% by weight, based on the total weight of the alkali-metal-chloride-containing solution. In contrast, the process according to the invention surprisingly offers the possibility of recycling by means of electrolysis significantly greater fractions of the alkali metal chloride situated in the reaction wastewater of the diaryl carbonate production, and thereby of utilizing it.

EMBODIMENTS OF THE INVENTION

An embodiment of the present invention is a process for producing diaryl carbonate and the processing of at least a part of the resulting alkali-metal-chloride-containing solution in a downstream alkali metal chloride electrolysis comprising:
  a) producing phosgene by reacting chlorine with carbon monoxide;
  b) reacting said phosgene with at least one monophenol in the presence of a base and optionally basic catalyst to form a diaryl carbonate and an alkali-metal-chloride-containing solution;
  c) separating off and working up said diaryl carbonate;
  d) separating off said alkali-metal-chloride-containing solution from solvent residues and optionally catalyst residues;
  e) electrochemically oxidizing at least a part of said alkali-metal-chloride-containing solution to form chlorine, alkali solution, and optionally hydrogen;
  f) recycling at least a part of said chlorine to a); and/or
  g) recycling at least a part of said alkali solution to b);
wherein said alkali-metal-chloride-containing solution has an alkali metal chloride content in the range of from 18 to 25% by weight based on the total weight of said alkali-metal-chloride-containing solution and/or at least a part of said alkali-metal-chloride-containing solution is recycled to b).

Another embodiment of the present invention is the above process, wherein said separation in d) is achieved by stripping said alkali-metal-chloride-containing solution with steam and treating it with an adsorbent, wherein said alkali-metal-chloride-containing solution is adjusted to a pH less than or equal to 8 before the treatment with said adsorbent.

Another embodiment of the present invention is the above process, wherein said absorbent is activated carbon.

Another embodiment of the present invention is the above process, wherein said base in b) is an alkali-metal-containing base.

Another embodiment of the present invention is the above process, wherein said alkali-metal-containing base is a sodium containing base and said alkali-metal-containing base and said monophenol are used in amounts such that the sodium phenolate content of the resultant solution of said alkali-metal-containing base and said monophenol is in the range of from 31 to 40% by weight sodium phenolate, based on the total weight of the solution.

Another embodiment of the present invention is the above process, wherein up to 80% by weight of said alkali-metal-chloride-containing solution from d) is recycled to b).

Another embodiment of the present invention is the above process, wherein up to 50% by weight of said alkali-metal-chloride-containing solution from d) is b).

Another embodiment of the present invention is the above process, wherein a gas diffusion electrode as cathode is used to achieve said electrochemical oxidation.

Another embodiment of the present invention is the above process, wherein at least a part of the purified alkali-metal-chloride-containing solution from d) is added to the brine circuit of a membrane electrolysis for producing chlorine, sodium hydroxide solution and optionally hydrogen.

Another embodiment of the present invention is the above process, wherein additional alkali metal chloride is added to the alkali-metal-chloride-containing solution in e) so as to elevate the alkali metal chloride concentration.

Another embodiment of the present invention is the above process, wherein said alkali-metal-chloride-containing solution is adjusted to a pH of less than 7 before the treatment with said adsorbent.

Another embodiment of the present invention is the above process, wherein the pH of said alkali-metal-chloride-containing solution is adjusted with hydrochloric acid or hydrogen chloride.

Another embodiment of the present invention is the above process, wherein ion-exchange membranes are used in e), wherein the water transport per mole of sodium is greater than 4 mol of $H_2O$/mole of sodium.

Another embodiment of the present invention is the above process, wherein the water transport per mole of sodium is in the range of from 5.5 to 6.5 mol of $H_2O$/mole of sodium.

Another embodiment of the present invention is the above process, wherein said monophenol is phenol, a $C_1$-$C_9$-alkylphenol, or a halophenol.

Another embodiment of the present invention is the above process, wherein said $C_1$-$C_9$-alkylphenol is selected from the group consisting of cresols, p-tert-butylphenol, p-cumylphenol, p-n-octylphenol, p-isooctylphenol, p-n-nonylphenol, and p-isononylphenol.

Another embodiment of the present invention is the above process, wherein said halophenol is selected from the group consisting of p-chlorophenol, 2,4-dichlorophenol, p-bromophenol, and 2,4,6-tribromophenol.

Another embodiment of the present invention is the above process, wherein said monophenol is phenol.

Another embodiment of the present invention is the above process, wherein cells are used in e) which comprise anodes and membranes, wherein said anodes have a higher surface area than that of said membranes.

DESCRIPTION OF THE INVENTION

The invention relates to a process for production of diaryl carbonate and processing of at least a part of the resultant alkali-metal-chloride-containing solution in a downstream alkali metal chloride electrolysis which comprises the following steps:
a) producing phosgene by reacting chlorine with carbon monoxide, and
b) reacting the phosgene formed according to step a) with at least one monophenol in the presence of a base and optionally basic catalyst to give a diaryl carbonate and an alkali-metal-chloride-containing solution, and
c) separating off and working up the diaryl carbonate formed in step b), and
d) separating off the alkali-metal-chloride-containing solution remaining according to step c) from solvent residues and optionally catalyst residues, in particular by stripping the solution with steam, and treating it with adsorbents, in particular with activated carbon, wherein, before the treatment with adsorbents, the alkali-metal-chloride-containing solution is adjusted to a pH less than or equal to 8, and
e) electrochemically oxidizing at least a part of the alkali-metal-chloride-containing solution from d) with formation of chlorine, alkali solution and optionally hydrogen, and
f) recycling at least a part of the chlorine produced according to step e) to the production of phosgene according to step a) and/or
g) recycling at least a part of the alkali solution produced according to step e) to the production of diaryl carbonate according to step b), characterized in that the alkali-metal-chloride-containing solution produced in step b) has an alkali metal chloride content of 18 to 25% by weight based on the total weight of the alkali-metal-chloride-containing solution and/or at least a part of the alkali-metal-chloride-containing solution occurring in step d) is recycled to step b).

The elevated alkali metal chloride content of 18 to 25% by weight, which is based on the total weight of the alkali-metal-chloride-containing solution and is desirable for the electrolysis in the process according to the invention can be achieved in that in step b), the base is an alkali-metal-containing base, preferably a sodium-containing base, and this alkali-metal-containing base and monophenol are used in amounts such that the sodium phenolate content of the resultant solution of alkali-metal-containing base and monophenol is 31 to 40% by weight sodium phenolate, based on the total weight of the solution, and/or at least a part of the alkali-metal-chloride-containing solution occurring in step d) is recycled to step b). In this case, preferably up to 80% by weight, preferably up to 50% by weight, of the alkali-metal-chloride-containing solution occurring in step d) can be recycled to step b).

In the event that at least a part of the alkali-metal-chloride-containing solution occurring in step d) is recycled to step b), in preferred embodiments of the process according to the invention, the alkali-metal-chloride-containing solution remaining according to step c) can, in addition combined at least in part with wash water from the workup of the diaryl carbonate according to step c), be used in step d). This procedure offers the additional advantage that complete disposal of the wash phases can be avoided.

Preferably, in step b), the sodium phenolate content of the resultant solution of alkali-metal-containing base and monophenol of 31 to 40% by weight of sodium phenolate is achieved by reacting a monophenol with a 14 to 21% by weight strength alkali-metal-containing base, in particular a sodium-containing base.

Particularly suitable monophenols for use in the novel process are phenols of the formula (I)

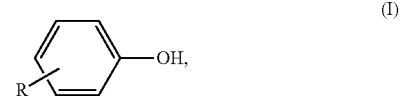

where
R is hydrogen, halogen or a branched or unbranched $C_1$- to $C_9$-alkyl radical or alkoxycarbonyl radical.

$C_1$-$C_9$-alkyl, in the context of the invention, is, for example and preferably, methyl, ethyl, n-propyl, isopropyl, n-butyl, sec-butyl, tert-butyl, n-pentyl, 1-methylbutyl, 2-methylbutyl, 3-methylbutyl, neopentyl, 1-ethylpropyl, cyclohexyl, cyclopentyl, n-hexyl, n-heptyl, n-octyl, isooctyl, n-nonyl, isononyl.

Halogen in the context of the invention, is, for example and preferably, fluorine, chlorine, bromine or iodine, preferably chlorine or bromine.

Preferred suitable monophenols are therefore phenol, alkylphenols such as cresols, p-tert-butylphenol, p-cumylphenol, p-n-octylphenol, p-isooctylphenol, p-n-nonylphenol and p-isononylphenol, halophenols, such as p-chlorophenol, 2,4-dichlorophenol, p-bromophenol and 2,4,6-tribromophenol or salicylic acid methyl ester. Particular preference is given to phenol.

Suitable bases for the reaction of the monophenol with phosgene are, for example, alkali metal salts, preferably alkali metal hydroxides, such as, for example, Na, K or Li hydroxide, particularly preferably sodium hydroxide solution. The base is used in the process according to the invention preferably as 14 to 21% strength by weight aqueous solution.

The reaction in step b) can be accelerated by basic catalysts such as tertiary amines, N-alkylpiperidines or onium salts. Preference is given to nitrogenous catalysts. Particular preference is given to tributylamine, triethylamine and N-ethylpiperidine.

The basic catalyst used can be open-chain or cyclic, particular preference is given to triethylamine and ethylpiperidine. The catalyst is used in the process according to the invention preferably as 1 to 55% strength by weight solution.

Onium salts, in the context of the invention, are preferably taken to mean compounds such as $NR_4X$, wherein the radicals R, independently of one another, can be H and/or an alkyl and/or aryl radical and X is an anion, such as, for example, chloride, bromide or iodide.

Phosgene can be used in step b) in the liquid state, gaseous state or dissolved in an inert solvent.

In the process according to the invention, in step b), inert organic solvents which are preferably usable are, preferably, aromatic solvents, halogenated, more preferably chlorinated, aliphatic or aromatic solvents, or mixtures of these. These are, for example, toluene, dichloromethane, the various dichloroethane and chloropropane compounds, chlorobenzene and chlorotoluene or mixtures of these. Particular preference is given to dichloromethane.

Diarylcarbonates which are produced in step b) in the process according to the invention are preferably those of the general formula (II)

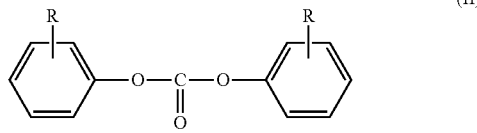

where R has the meaning stated for formula (I). Particularly preferably, diphenyl carbonate is produced by the process according to the invention.

The reaction procedure for step b) proceeds preferably continuously and particularly preferably in plug flow without great backmixing. This can be achieved, for example, in tubular reactors. The mixing of the two phases (aqueous and organic phase) can be effected, for example, by built-in pipe baffles, static mixers and/or pumps.

The reaction according to step b) proceeds particularly preferably in two stages.

In the first stage of the preferred process, the reaction is started by combining the starting materials phosgene, at least one inert organic solvent which preferably first acts as solvent for the phosgene, and the monophenol, which is preferably already dissolved in advance in the solution of the base, preferably in the alkali solution. The residence time is typically in the first stage in the range from 2 seconds to 300 seconds, particularly preferably in the range from 4 seconds to 200 seconds. The pH of the first stage is adjusted by the ratio of base (preferably alkali solution)/mono-phenol/phosgene preferably in such a manner that the pH is in the range from 11.0 to 12.0, preferably 11.2 to 11.8, particularly preferably 11.4 to 11.6. The reaction temperature of the first stage is maintained by cooling preferably below 40° C., particularly preferably at 35° C. or below.

In the second stage of the preferred process, the reaction to give the diaryl carbonate is completed. The residence time in the preferred process is 1 minute to 2 hours, preferably 2 minutes to 1 hour, very particularly preferably 3 minutes to 30 minutes. The second stage of the preferred process is controlled by permanent monitoring of the pH, which, in the continuous process, is measured preferably online by processes which are known in principle, and corresponding adjustment of the pH by addition of alkali solution. The amount of base supplied, preferably the alkali solution, is, in particular, set in such a manner that the pH of the reaction mixture in the second process stage is in the range from 7.5 to 10.5, preferably 8 to 9.5, very particularly preferably 8.2 to 9.3. The reaction temperature of the second stage is maintained by cooling at preferably below 50° C., particularly preferably below 40° C., very particularly preferably 35° C. or below. The alkali-metal-chloride-containing solution produced in step b) therefore, immediately after the reaction to give the diaryl carbonate is completed, has a temperature of below 50° C., particularly preferably below 40° C., very particularly preferably 35° C. or below.

The general parameters and/or explanations listed in this application, or listed in preferred ranges, can also be combined among one another, that is to say between the respective ranges and preferred ranges as desired.

In preferred embodiments of the process according to the invention, in step b), phosgene is used in the molar ratio of 1:2 to 1:2.2 with respect to the monophenol. The inert organic solvent is added in such a manner that the diaryl carbonate, after the reaction, is present in a 5 to 50% strength by weight solution, preferably 20 to 45% strength by weight solution, based on the organic phase.

The optionally used catalyst is preferably added in amounts of 0.0001 mol to 0.1 mol, based on the monophenol used.

After the reaction b), in step c), preferably the organic phase containing the diaryl carbonate is usually washed with an aqueous liquid and, after each washing operation, separated as far as possible from the aqueous phase. As wash liquid, use is made of aqueous liquids for separating off the catalyst, e.g. dilute mineral acids such as HCl or $H_3PO_4$, and for further purification, demineralized water is used. The concentration of HCl or $H_3PO_4$ in the wash liquid can preferably be 0.5 to 1.0% by weight. The organic phase is washed, for example and preferably, twice.

Phase separation devices which can be used for separating off the wash liquid from the organic phase are fundamentally known separation vessels, phase separators, centrifuges or coalescers or else combinations of these appliances.

This produces, without taking into account the solvent which is still to be separated off, surprisingly high degrees of purity of the diaryl carbonate of >99.85%.

After the synthesis of the diaryl carbonate, the diaryl carbonate is separated off in the form of its solution in the inert organic solvent used in the production, for example methylene chloride.

To obtain ultrapure diaryl carbonate, the solvent is preferably evaporated. The evaporation can proceed in a plurality of evaporator stages. For example, this proceeds via one or more series-connected distillation columns in which the solvent is separated off from the diaryl carbonate.

This (these) purification stage(s) c) can be conducted, for example, continuously, in such a manner that the bottom temperature during the distillation is 150° C. to 310° C., preferably 160 to 230° C. The pressure used for carrying out this distillation is, in particular, 1 to 1000 mbar, preferably 5 to 100 mbar.

The diaryl carbonates thus purified are distinguished by particularly high purity (according to GC analysis >99.95%) and extremely good transesterification behaviour, such that they are suitable for subsequent production of polycarbonates of excellent quality. The use of diaryl carbonates for producing aromatic oligo/poly-carbonates by the melt transesterification process is known from the literature and is described, for example, in the Encyclopedia of Polymer Science, Vol. 10 (1969), Chemistry and Physics of Polycarbonates, Polymer Reviews, H. Schnell, Vol. 9, John Wiley and Sons, Inc. (1964) or U.S. Pat. No. 5,340,905.

The aqueous alkali-metal-chloride-containing solution remaining after the phase separation in the context of the separation according to step c)—hereinafter also termed alkali-metal-chloride-containing wastewater—is advantageously freed from readily volatile organic impurities such as, for example, residues of the organic solvent used in the synthesis and if appropriate catalyst residues, for example by distillation or steam stripping. In this case there remains an alkali-metal-chloride-containing solution having a high content of dissolved alkali metal chloride of 18 to 25% by weight based on the total weight of the alkali-metal-chloride-containing solution which additionally further contains dissolved alkali metal carbonates in an amount of 0.3 to 1.5% by weight, based on the total weight of the alkali-metal-chloride-containing solution. These alkali metal carbonates can have formed, for example, by hydrolysis of the phosgene as a side reaction of the diaryl carbonate production. In addition, the alkali-metal-chloride-containing wastewater is polluted with organic compounds, e.g. with phenols (e.g. unsubstituted phenol, alkylphenols).

Subsequently, the prepurified alkali-metal-chloride-containing wastewater is treated with adsorbents, preferably with activated carbon. Before this treatment with adsorbents, the alkali-metal-chloride-containing wastewater is adjusted to a pH less than or equal to 8, preferably to a pH of less than 7.

This reduction of the pH in process step d) proceeds preferably via addition of protic acids. More preferably the reduction of pH in process step d) is carried out using hydrochloric acid or gaseous hydrogen chloride. The use of the cheaper sulphuric acid which is conceivable in principle, but is undesirable in the present process, would lead to sodium sulphate being formed on the pH reduction, which sodium sulphate would accumulate in the anolyte circuit in the subsequent electrolysis. Since, for example, the ion-exchange membranes according to the manufacturer's instructions must only be operated up to a certain sodium sulphate concentration in the anolyte, more anolyte would have to be discharged than when hydrochloric acid or hydrogen chloride is used, the reaction product of which, in addition, is again advantageously the desired sodium chloride.

At least at least a part of the alkali-metal-chloride-containing wastewater from step d) is subsequently subjected to an electrochemical oxidation, preferably in the form of an alkali metal chloride electrolysis with formation of chlorine, alkali solution and if appropriate hydrogen.

The alkali metal chloride electrolysis process is described in more detail hereinafter. The description hereinafter must be considered as an example with respect to the electrolysis of sodium chloride, since in the process, as already stated above, in principle any alkali metal chloride can be used (in particular LiCl, NaCl, KCl). Since the use of sodium chloride or sodium hydroxide solution in the preceding stages of the process according to the invention is preferred, however, the electrolysis of sodium chloride is also the preferred embodiment of the process according to the invention.

Conventionally, e.g., for the electrolysis of sodium-chloride-containing solutions, use is made of membrane electrolysis processes (see in this context Peter Schmittinger, CHLORINE, Wiley-VCH Verlag, 2000). In this case an electrolysis cell divided into two is used which consists of an anode chamber having an anode and a cathode chamber having a cathode. Anode chamber and cathode chamber are separated by an ion-exchange membrane. A sodium-chloride-containing solution having a sodium chloride concentration of conventionally more than 300 g/l is introduced into the anode chamber. At the anode the chloride ion is oxidized to chlorine which is conducted from the cell together with the depleted sodium-chloride-containing solution. The sodium ions migrate under the influence of the electric field through the ion-exchange membrane to the cathode chamber. During this migration, each mole of sodium, depending on the membrane, is accompanied by between 3.5 and 4.5 mol of water. This leads to the fact that the anolyte is depleted in water. In contrast to the anolyte, on the cathode side, as a result of the electrolysis of water to hydroxide ions and hydrogen, water is consumed. The water passing together with the sodium ions into the catholyte is sufficient in order to keep the sodium hydroxide concentration in the outlet to 31 to 32% by weight—at an inlet concentration of 30% and a current density of 4 kA/m$^2$. In the cathode chamber water is electrochemically reduced, with hydroxide ions and hydrogen being formed.

Alternatively, as cathode, use can also be made of a gas-diffusion electrode, at which oxygen is reacted with electrons to give hydroxide ions, wherein no hydrogen is formed. Together with the sodium ions which have passed into the cathode chamber through the ion-exchange membrane, the hydroxide ions form sodium hydroxide solution. Conventionally, a sodium hydroxide solution having a concentration of 30% by weight is fed into the cathode chamber and a sodium hydroxide solution having a concentration of 31 to 32% by weight is removed. The purpose is to achieve a concentration of sodium hydroxide solution as high as possible, since conventionally the sodium hydroxide solution is stored or transported as 50% strength by weight alkali solution. However, commercially available membranes are not currently stable towards an alkali solution having a concentration higher than 32% by weight, such that the sodium hydroxide solution produced must subsequently be concentrated by thermal evaporation.

In the case of the sodium chloride electrolysis in the context of the process according to the invention, additional water is introduced into the anolyte via the use of the sodium-chloride-containing wastewater, but only water is discharged into the catholyte via the membrane. If more water is introduced via the sodium-chloride-containing solution than can be transported to the catholyte, the anolyte is depleted in sodium chloride and the electrolysis can no longer be operated continuously. At very low sodium chloride concentrations the side reaction of oxygen formation would start.

In order to feed maximum amounts of sodium-chloride-containing solutions economically to the sodium chloride electrolysis, it can be useful for the water transport via the membrane to be increased. This can be performed by a selection of suitable membranes, as described in U.S. Pat. No. 4,025,405. The effect of increased water transport is that the otherwise conventional water addition for maintenance of the alkali solution concentration can be dispensed with.

According to U.S. Pat. No. 3,773,634, at high water transport through the membrane, the electrolysis can be operated when an alkali solution concentration of 31 to 43% by weight and a sodium chloride concentration of 120 to 250 g/l are used.

A disadvantage of both processes is the lower current yield of these processes.

According to the process of the invention, the separation c) of the sodium-chloride-containing wastewater proceeds by means of phase separation. Subsequently, in step d) the solvent and any catalyst used are removed, in particular by stripping with steam, and also after pH adjustment by a treatment with adsorbents. Hereafter, alkali-metal-chloride-containing wastewater can be fed directly to the electrolysis e).

In a preferred embodiment of the process according to the invention, water can additionally be withdrawn from the alkali-metal-chloride-containing wastewater via a concentration process, in order to increase the alkali metal chloride concentration. Therefore, preference is given to a process characterized in that the alkali-metal-chloride-containing solution from d), before the electrolysis e), is concentrated by means of membrane distillation processes or reverse osmosis. Compared with processes in which, in the diaryl carbonate production, only an alkali-metal-chloride-containing wastewater having an alkali metal chloride content of up to 17% by weight based on the total weight of the alkali-metal-chloride-containing solution is found, in the process according to the invention, however, significantly less water need be removed by the concentration process in order to achieve the same alkali metal chloride concentration.

In this case, for example, reverse osmosis or, particularly preferably, membrane distillation or membrane contactors can be used (see MELIN; RAUTENBACH, Membranverfahren [membrane processes]; SPRINGER, BERLIN, 2003). By a combination of operation of the electrolysis cell according to the invention and concentration processes, theoretically, up to 100% of the sodium chloride can be recovered from the wastewater.

In a further preferred embodiment of the process according to the invention, the alkali-metal-chloride-containing wastewater of the diaryl carbonate production is concentrated by solid alkali metal chloride and fed to the alkali metal chloride electrolysis. By means of this preferred embodiment of the process according to the invention, more than 50% of the alkali metal chloride from the wastewater of the diaryl carbonate production could be recycled and thereby reused. This assumes, however, that the chlorine and the alkali solution are not used exclusively for the diaryl carbonate production. Compared with processes in which, in the diaryl carbonate production, only an alkali-metal-chloride-containing wastewater having an alkali metal chloride content of up to 17% by weight based on the total weight of the alkali-metal-chloride-containing solution is found, in the process according to the invention, however, significantly less addition of solid alkali metal chloride is required for concentration.

The process according to the invention can also be carried out using an alkali-metal-chloride electrolysis in which no hydrogen is generated at the cathode, but the cathode is replaced by a gas-diffusion electrode at which oxygen is reduced to hydroxide ions. If, for example, in an integrated site, hydrogen is not required for chemical reactions, it is possible to avoid the automatically produced product hydrogen. The advantage is energy savings in the electrolysis which is due to the lower electrolysis voltage when a gas-diffusion electrode is used.

The alkali metal chloride electrolysis should customarily be operated in such a manner that the alkali metal chloride concentration of the alkali metal chloride solution passing from the cell is between 100 and 280 g/l of sodium chloride and/or that the concentration of the alkali solution which passes out of the cell is 13 to 33% by weight. Particular preference is given to concentrations which enable the operation of the cell at lower voltages. For this the concentration of the alkali metal chloride solution passing out of the cell should preferably be between 110 to 220 g/l of alkali metal chloride and/or the concentration of the alkali solution which passes out of the cell should be 20 to 30% by weight. In a preferred embodiment of the process according to the invention, the alkali metal chloride electrolysis is operated in such a manner that the alkali metal chloride solution which passes out of the cell has an NaCl concentration of less than 200 g/l. In parallel hereto, the alkali solution concentration running out of the cell can be less than 30% by weight.

The water transport through the membrane does not depend only on the operating parameters, but also on the membrane type used. According to the process of the invention, preferably, those ion-exchange membranes are used which, under the conditions of sodium chloride and alkali solution concentration according to the invention, enable water transport through the membrane of more than 4.5 mol of water per mole of sodium.

The current density in this case is calculated according to the membrane area and is in particular 2 to 6 kA/m$^2$. Particularly preferably, anodes having a relatively large surface area are used. Anodes having a relatively large surface area are taken to mean those in which the physical surface area is significantly greater than the geometric, i.e. projected, surface area. Anodes having a relatively high surface area are, for example, electrodes which have a foam-like or felt-like structure. As a result, anodically, a very high electrode surface area is offered and the local current density is greatly reduced. The surface area of the anode may preferably be selected in such a manner that the local current density, based on the physical surface area of the electrode, is less than 3 kA/m$^2$. The higher the surface area and the lower the local current density, the lower the alkali metal chloride concentration in the brine which can be selected and the higher the fraction of alkali metal chloride from the wastewater which can be recycled.

The pH of the alkali-metal-chloride-containing wastewater should, before the electrolysis e), be preferably less than 7, particularly preferably be 0.5 to 6. The pH adjustment can proceed by addition of proton acids, preferably hydrochloric acid or gaseous hydrogen chloride.

The ion-exchange membranes used in the electrolysis should preferably exhibit a water transport per mole of sodium of more than 4.0 mol of $H_2O$/mole of sodium, particularly preferably 5.5 to 6.5 mol of $H_2O$/mole of sodium.

The process is preferably operated in such a manner that the electrolysis e) is operated at a temperature of 70 to 100° C., preferably 80 to 95° C.

The electrolysis is operated at an absolute pressure of 1 to 1.4 bar, preferably at one from 1.1 to 1.2 bar. The pressure conditions between anode chamber and cathode chamber are selected, in particular, in such a manner that the pressure in the cathode chamber is higher than the pressure in the anode chamber. The differential pressure between cathode chamber and anode chamber, in a particularly preferred process, should be 20 to 150 mbar, preferably 30 to 100 mbar.

At low alkali metal chloride concentrations, special anode coatings can also be used. In particular, the coating of the anode, in addition to ruthenium oxide, can also contain other noble metal components of subgroups 7 and 8 of the Periodic Table of the Elements. For example, the anode coating can be doped with palladium compounds. Likewise, coatings based on diamonds are usable.

The sodium-chloride-containing solution (sodium-chloride-containing wastewater) conventionally obtained from diphenyl carbonate production (DPC production) according to known processes has a sodium chloride content of up to 17% by weight, provided that it is the reaction wastewater. If the reaction wastewater is additionally combined with the wash water from the workup according to step c), the NaCl concentration is, for example, only approximately 13% by weight. If the electrolysis delivers the chlorine and the sodium hydroxide solution exclusively for DPC production, only a small part of the sodium-chloride-containing wastewater can be used in the electrolysis. For instance, with the conventional ion-exchange membranes and the standard operating parameters of sodium chloride electrolysis, only a maximum of 26% of the sodium chloride of a 17% strength by weight sodium-chloride-containing DPC wastewater can be used. The standard operating parameters of NaCl electrolysis are a brine concentration in the outlet of 200 to 240 g/l and an NaOH concentration of 31 to 32% by weight. Complete recycling of the sodium chloride which is produced is therefore not possible to date. Concentration by thermal evaporation of the water is, in addition, currently not economic, since sodium chloride is available as a very cheap product.

Using the process according to the invention, now, significantly more than 26% of the sodium chloride from wastewaters which arise, at an NaCl content of 18 to 25% by weight, can be recycled, provided that the sodium chloride electrolysis provides exclusively the chlorine and sodium hydroxide solution for DPC production. Conventionally, sodium chloride electrolyses are operated at integrated chemical sites having a plurality of chlorine consumers, so that a sodium-chloride-containing solution for recycling is not provided by all consumers. The fraction of reutilizable sodium chloride from the wastewater further increases, in addition, when the sodium chloride electrolysis must provide sodium hydroxide solution and chlorine not exclusively for diaryl carbonate production.

Compared with the prior art (WO 03/70639 A1), in which a maximum of 26% of the sodium chloride present in the wastewater of the DPC production can be used in NaCl electrolysis, by means of the process according to the invention, more than 26% of the sodium chloride from the wastewater can be recovered.

The examples hereinafter are intended to illustrate the present invention, but without restricting it.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

The examples are intended to present the process according to the invention with reference to the sodium-chloride-containing wastewater arising in the production of diphenyl carbonate (DPC production).

Example 1

Addition of Enriched Sodium-Chloride-Containing Reaction Wastewater to the Sodium Chloride Electrolysis—Addition of a 22.5% Strength by Weight Sodium Chloride Solution from the DPC Production to the Sodium Chloride Electrolysis a) Isolation of the Production Wastewater from DPC Production In a vertically upright cooled tubular reactor, a mixture of 145.2 kg/h of 14.5% strength sodium hydroxide solution produced by diluting 65.8 kg/h of a 32% strength sodium hydroxide solution with 79.4 kg/h of demineralized water, and 48.3 kg/h of phenol was continuously combined with a solution of 86.2 kg/h of methylene chloride and 27.5 kg/h of phosgene (8 mol % excess based on phenol). This reaction mixture was cooled to a temperature of 33° C. and after a median residence time of 15 seconds, a pH of 11.5 was measured. Then, in the second stage of the process, to this reaction mixture was added 5.4 kg/h of 50% strength NaOH, so that the pH of the second reaction stage, after a further residence time of 5 minutes, was 8.5. In the continuously operated reaction, metering fluctuations which occurred were contained by respective adaptations of the NaOH feeds. In the second stage of the process, the reaction mixture was constantly mixed by passing it through a tube provided with constrictions. The reaction temperature, after repeated addition of NaOH, was set to 30° C. by cooling. After separating off the organic phase from the aqueous phase (reaction wastewater), the DPC solution was washed with 0.6% strength hydrochloric acid and water. After removal of the solvent, 99.9% pure diphenyl carbonate was obtained. The reaction wastewater was combined with the wash phases and freed from solvent residues and catalyst by stripping with steam. After neutralization with hydrochloric acid and treatment with activated carbon, the production wastewater contained 13.2% by weight NaCl and less than 2 ppm of phenol.

It could be recycled to the production process without further purification.

b) Sodium Chloride Enrichment in the Wastewater by Recycling the Wastewater from a) to the DPC Production DPC production was carried out as described in Example 1, but instead of 79.4 kg/h of demineralized water, continuously a mixture of 37.9 kg/h of demineralized water and 47.7 kg/h of the production wastewater obtained according to Example 1a) was used.

After separating off the organic phase from the aqueous phase (reaction wastewater), the organic phase was washed with 0.6% strength hydrochloric acid and water. After removal of the solvent, 99.9% pure diphenyl carbonate was obtained. The reaction wastewater was, without prior combination with the wash phases, freed from solvent residues and catalyst by stripping with steam. After neutralization with hydrochloric acid and treatment with activated carbon, the reaction wastewater contains 22.5% by weight NaCl and less than 2 ppm of phenol.

c) Electrochemical Oxidation of the Reaction Wastewater from b)

The electrolysis was carried out by way of example in a laboratory electrolysis cell having an anode surface area of 0.01 m$^2$. The current density was 4 kA/m$^2$, temperature of the outlet cathode side 88° C., temperature of the outlet anode side 89° C. An electrolysis cell having standard anode and cathode coating from DENORA, Germany was used. An ion-exchange membrane from DuPont, Nafion 982 WX, was used. The electrolysis voltage was 3.02 V. A sodium-chloride-containing solution was circulated through the anode chamber by pumping at a mass flow rate of 0.96 kg/h. The concentration of the solution fed to the anode chamber was 25% by weight NaCl. From the anode chamber, a 20% strength by weight NaCl solution was taken off. 0.14 kg/h of 22.5% strength by weight reaction wastewater from the diphenyl carbonate production under b) and 0.0543 kg/h of solid sodium chloride were added to the NaCl solution taken off from the anode chamber. The solution was subsequently again fed into the anode chamber. The water transport through the membrane was 3.8 mol of water per mole of sodium.

On the cathode side, a sodium hydroxide solution was recirculated at a mass flow rate of 0.849 kg/h. The concentration of the sodium hydroxide solution fed into the cathode side was 30% by weight NaOH, the sodium hydroxide solution taken off from the cathode side had a concentration of 32.1% NaOH. 0.186 kg/h of the 32.1% strength alkali solution was taken off from the volume stream, to the remainder was added 0.057 kg/h of water and it was recycled to the cathode element.

35.7% of the reacted sodium chloride originated from the reaction wastewater of the DPC production.

Example 2

Addition of Enriched Sodium-Chloride-Containing Production Wastewater to the Sodium Chloride Electrolysis—Addition of an 18.0% Strength by Weight Sodium Chloride Solution from the DPC Production to the Sodium Chloride Electrolysis a) Sodium Chloride Enrichment of Production Wastewater by Wastewater Recycling to the Production Process The procedure was followed as described in Example 1b) but the reaction wastewater was combined with the wash phases and subsequently freed from solvent residues and catalyst by stripping with steam. After neutralization with hydrochloric acid and treatment with activated carbon, the production wastewater contained 18.0% by weight NaCl and less than 2 ppm of organic impurities.

It could be fed without further purification to the electrochemical oxidation to chlorine.

b) Electrochemical Oxidation of the Enriched Production of Wastewater from a)

The electrolysis was carried out by way of example in a laboratory electrolysis cell having an anode surface area of 0.01 m². The current density was 4 kA/m², temperature of the outlet cathode side 88° C., temperature of the outlet anode side 89° C. An electrolysis cell having standard anode and cathode coating from DENORA, Germany was used. An ion-exchange membrane from DuPont, Nation 982 WX, was used. The electrolysis voltage was 3.02 V. A sodium-chloride-containing solution was circulated through the anode chamber by pumping at a mass flow rate of 0.96 kg/h. The concentration of the solution fed to the anode chamber was 25% by weight NaCl. From the anode chamber, a 20% strength by weight NaCl solution was taken off. 0.133 kg/h of 18% strength by weight production wastewater from the diphenyl carbonate production under a) and 0.062 kg/h of solid sodium chloride were added to the NaCl solution taken off from the anode chamber. The solution was subsequently again fed into the anode chamber. The water transport through the membrane was 3.8 mol of water per mole of sodium.

On the cathode side, a sodium hydroxide solution was recirculated at a mass flow rate of 0.849 kg/h. The concentration of the sodium hydroxide solution fed into the cathode side was 30% by weight NaOH, the sodium hydroxide solution taken off from the cathode side had a concentration of 32.2% NaOH. 0.185 kg/h of the 32.2% strength alkali solution was taken off from the volume stream, to the remainder was added 0.057 kg/h of water and it was recycled to the cathode element.

27.0% of the reacted sodium chloride originated from the DPC production wastewater.

Example 3

Addition of Enriched Sodium-Chloride-Containing Reaction Wastewater to the Sodium Chloride Electrolysis—Addition of a 22.3% Strength by Weight Sodium Chloride Solution from DPC Production to the Sodium Chloride Electrolysis a) Sodium Chloride Enrichment of Reaction Wastewater by Elevation of the Sodium Phenolate Concentration in the DPC Production The procedure was followed as described in example 1a), but instead of 79.4 kg/h, only 54.6 kg/h of demineralized water was used. After separating off the organic phase from the aqueous phase (reaction wastewater), the organic phase was washed with 0.6% strength hydrochloric acid and water. After removal of the solvent, 99.9% pure diphenyl carbonate was obtained. The reaction wastewater, without prior combination with the wash phases, was freed from solvent residues and catalyst by stripping with steam. After neutralization with hydrochloric acid and treatment with activated carbon, the reaction wastewater contained 22.3% by weight NaCl and less than 2 ppm of phenol.

b) Electrochemical Oxidation of the Enriched Reaction Wastewater from a)

The electrolysis was carried out by way of example in a laboratory electrolysis cell having an anode surface area of 0.01 m². The current density was 4 kA/m², temperature of the outlet cathode side 88° C., temperature of the outlet anode side 89° C. An electrolysis cell having standard anode and cathode coating from DENORA, Germany was used. An ion-exchange membrane from DuPont, Nation 982 WX, was used. The electrolysis voltage was 3.02 V. A sodium-chloride-containing solution was circulated through the anode chamber by pumping at a mass flow rate of 0.96 kg/h. The concentration of the solution fed to the anode chamber was 25% by weight NaCl. From the anode chamber, a 20% strength by weight NaCl solution was taken off. 0.14 kg/h of 22.3% strength by weight reaction wastewater from the diphenyl carbonate production under a) and 0.0546 kg/h of solid sodium chloride were added to the NaCl solution taken off from the anode chamber. The solution was subsequently again fed into the anode chamber. The water transport through the membrane was 3.8 mol of water per mole of sodium.

On the cathode side, a sodium hydroxide solution was recirculated at a mass flow rate of 0.849 kg/h. The concentration of the sodium hydroxide solution fed into the cathode side was 30% by weight NaOH, the sodium hydroxide solution taken off from the cathode side had a concentration of 32.2% NaOH. 0.186 kg/h of the 32.2% strength alkali solution was taken off from the volume stream, to the remainder was added 0.057 kg/h of water and it was recycled to the cathode element.

35.3% of the reacted sodium chloride originated from the DPC reaction wastewater.

Comparative Example

Addition of Sodium-Chloride-Containing Reaction Wastewater to the Sodium Chloride Electrolysis—Addition of a 17% Strength by Weight Sodium Chloride Solution from DPC Production a) Isolation of the Reaction Wastewater from DPC Production In a vertically upright cooled tubular reactor, a mixture of 145.2 kg/h of 14.5% strength sodium hydroxide solution produced by diluting 65.8 kg/h of a 32% strength sodium hydroxide solution with 79.4 kg/h of demineralized water, and 48.3 kg/h of phenol was continuously combined with a solution of 86.2 kg/h of methylene chloride and 27.5 kg/h of phosgene (8 mol % excess based on phenol). This reaction mixture was cooled to a temperature of 33° C. and after a median residence time of 15 seconds, a pH of 11.5 was measured. Then, in the second stage of the process, to this reaction mixture was added 5.4 kg/h of 50% strength NaOH, so that the pH of the second reaction stage, after a further residence time of 5 minutes, was 8.5. In the continuously operated reaction, metering fluctuations which occurred were contained by respective adaptations of the NaOH feeds. In the second stage of the process, the reaction mixture was constantly mixed by passing it through a tube provided with constrictions. The reaction temperature, after repeated addition of NaOH, was set to 30° C. by cooling. After separating off the organic phase from the aqueous phase (reaction wastewater), the DPC solution was washed with 0.6% strength hydrochloric acid and water. After removal of the solvent, 99.9% pure diphenyl carbonate was obtained. The reaction wastewater was combined with the wash phases and freed from solvent residues and catalyst by stripping with steam. After neutralization with hydrochloric acid and treatment with activated carbon, the reaction wastewater contained 17% by weight NaCl and less than 2 ppm of phenol.

It could be fed to the sodium chloride electrolysis cell without further purification.

b) Electrochemical Oxidation of the Reaction Wastewater from a)

The electrolysis was carried out by way of example in a laboratory electrolysis cell having an anode surface area of 0.01 m$^2$. The current density was 4 kA/m$^2$, temperature of the outlet cathode side 88° C., temperature of the outlet anode side 89° C. An electrolysis cell having standard anode and cathode coating from DENORA, Germany was used. An ion-exchange membrane from DuPont, Nafion 982 WX, was used. The electrolysis voltage was 3.02 V. A sodium-chloride-containing solution was circulated through the anode chamber by pumping at a mass flow rate of 0.98 kg/h. The concentration of the solution fed to the anode chamber was 25% by weight NaCl. From the anode chamber, a 20% strength by weight NaCl solution was taken off. 0.121 kg/h of 17% strength by weight reaction wastewater from the diphenyl carbonate production from Example 1a) and 0.0653 kg/h of solid sodium chloride were added to the NaCl solution taken off from the anode chamber. The solution was subsequently again fed into the anode chamber. The water transport through the membrane was 3.5 mol of water per mole of sodium.

On the cathode side, a sodium hydroxide solution was recirculated at a mass flow rate of 1.107 kg/h. The concentration of the sodium hydroxide solution fed into the cathode side was 30% by weight NaOH, the sodium hydroxide solution taken off from the cathode side had a concentration of 32% NaOH. 0.188 kg/h of the 31.9% strength alkali solution was taken off from the volume stream, to the remainder was added 0.0664 kg/h of water and it was recycled to the cathode element.

Only 23.3% of the reacted sodium chloride originated from the DPC reaction wastewater.

The preceding Examples 1 to 3 according to the invention show, compared with the comparative example, that by concentrating the sodium-chloride-containing waste-water, not only does the fraction of the sodium chloride which originates from the DPC production and is converted during the subsequent electrolysis significantly increase, but also the amount of the sodium chloride which must be additionally added in solid form before the electrolysis can be significantly decreased. This results in a significantly better utilization of the sodium chloride in the wastewater and smaller amounts of salt-polluted process wastewaters to be disposed of.

The invention claimed is:

1. A process for producing diaryl carbonate and processing of at least a part of a resulting alkali-metal-chloride-containing solution in a downstream alkali metal chloride electrolysis comprising:
   a) producing phosgene by reacting chlorine with carbon monoxide;
   b) reacting said phosgene with at least one monophenol in the presence of a base and optionally basic catalyst to form a diaryl carbonate and an alkali-metal-chloride-containing solution;
   c) separating off and working up said diaryl carbonate;
   d) separating off said alkali-metal-chloride-containing solution from solvent residues and optionally catalyst residues;
   e) electrochemically oxidizing at least a part of said separated alkali-metal-chloride-containing solution to form chlorine, alkali solution, and optionally hydrogen;
   f) recycling at least a part of said chlorine to a); and/or
   g) recycling at least a part of said alkali solution to b);
   wherein at least a part of said separated alkali-metal-chloride-containing solution is recycled to b).

2. The process of claim 1, wherein said separation in d) is achieved by stripping said alkali-metal-chloride-containing solution with steam and treating said alkali-metal-chloride-containing solution with an adsorbent, wherein said alkali-metal-chloride-containing solution is adjusted to a pH less than or equal to 8 before the treatment with said adsorbent.

3. The process of claim 2, wherein said absorbent is activated carbon.

4. The process of claim 2, wherein said alkali-metal-chloride-containing solution is adjusted to a pH of less than 7 before the treatment with said adsorbent.

5. The process of claim 4, wherein the pH of said alkali-metal-chloride-containing solution is adjusted with hydrochloric acid or hydrogen chloride.

6. The process of claim 1, wherein said base in b) is an alkali-metal-containing base.

7. The process of claim 6, wherein said alkali-metal-containing base is a sodium containing base and said alkali-metal-containing base and said monophenol are used in amounts such that the formed alkali-metal-chloride-containing solution has a sodium phenolate content in the range of from 31 to 40% by weight sodium phenolate, based on the total weight of the alkali-metal-chloride-containing solution.

8. The process of claim 1, wherein up to 80% by weight of said separated alkali-metal-chloride-containing solution from d) is recycled to b).

9. The process of claim 8, wherein up to 50% by weight of said separated alkali-metal-chloride-containing solution from d) is recycled to b).

10. The process of claim 1, wherein a gas diffusion electrode as cathode is used to achieve said electrochemical oxidation.

11. The process of claim 1, wherein the electrochemical oxidation of step e) is carried out by way of a membrane electrolysis with a brine circuit and at least a part of the separated alkali-metal-chloride-containing solution from d) is added to the brine circuit of the membrane electrolysis.

12. The process of claim 1, wherein alkali metal chloride is added to the alkali-metal-chloride-containing solution in e) so as to elevate the alkali metal chloride concentration.

13. The process of claim 1, wherein ion-exchange membranes are used in e), wherein the ion-exchange membranes exhibit a water transport per mole of sodium greater than 4 mol of H$_2$O/mole of sodium.

14. The process of claim 13, wherein the water transport per mole of sodium is in the range of from 5.5 to 6.5 mol of H$_2$O/mole of sodium.

15. The process of claim 1, wherein said monophenol is phenol, a C$_1$-C$_9$-alkylphenol, or a halophenol.

16. The process of claim 15, wherein said C$_1$-C$_9$-alkylphenol is selected from the group consisting of cresols, p-tert-butylphenol, p-cumylphenol, p-n-octylphenol, p-isooctylphenol, p-n-nonylphenol, and p-isononylphenol.

17. The process of claim 15, wherein said halophenol is selected from the group consisting of p-chlorophenol, 2,4-dichlorophenol, p-bromophenol, and 2,4,6-tribromophenol.

18. The process of claim 15, wherein said monophenol is phenol.

19. The process of claim 1, wherein cells are used in e) which comprise anodes and membranes, wherein said anodes have a higher surface area than that of said membranes.

* * * * *